(12) United States Patent
Muller et al.

(10) Patent No.: US 11,207,152 B2
(45) Date of Patent: Dec. 28, 2021

(54) SURGEON SUPPORT SYSTEM

(71) Applicants: Leah Muller, San Francisco, CA (US); Scott Beyer, San Francisco, CA (US)

(72) Inventors: Leah Muller, San Francisco, CA (US); Scott Beyer, San Francisco, CA (US)

(*) Notice: Subject to any disclaimer, the term of this patent is extended or adjusted under 35 U.S.C. 154(b) by 0 days.

(21) Appl. No.: 16/775,595

(22) Filed: Jan. 29, 2020

(65) Prior Publication Data
US 2020/0237474 A1 Jul. 30, 2020

Related U.S. Application Data

(60) Provisional application No. 62/798,458, filed on Jan. 29, 2019.

(51) Int. Cl.
| A47C 9/00 | (2006.01) |
| A47C 7/50 | (2006.01) |
| A47C 16/04 | (2006.01) |
| A61B 90/60 | (2016.01) |
| A47C 7/00 | (2006.01) |
| A47C 4/28 | (2006.01) |
| A47C 3/20 | (2006.01) |

(52) U.S. Cl.
CPC ............. *A61B 90/60* (2016.02); *A47C 3/20* (2013.01); *A47C 4/28* (2013.01); *A47C 7/006* (2013.01); *A47C 7/5068* (2018.08); *A47C 9/005* (2013.01); *A47C 16/04* (2013.01)

(58) Field of Classification Search
CPC .................................................... A47C 9/005
USPC ....................................... 297/423.11, 423.12
See application file for complete search history.

(56) References Cited

U.S. PATENT DOCUMENTS

| 3,754,787 | A | * | 8/1973 | Garber | ................... | A61B 90/60 |
| | | | | | | 297/195.11 |
| 4,650,249 | A | * | 3/1987 | Serber | ................... | A47C 9/005 |
| | | | | | | 297/423.11 X |
| 5,251,961 | A | * | 10/1993 | Pass | ....................... | A47C 9/005 |
| | | | | | | 297/423.1 |
| 5,401,078 | A | * | 3/1995 | Riach | ..................... | A47C 7/503 |
| | | | | | | 297/423.11 X |
| 5,487,590 | A | * | 1/1996 | Haynes | ................ | A61G 15/007 |
| | | | | | | 297/195.11 |

(Continued)

FOREIGN PATENT DOCUMENTS

| DE | 202016003249 U1 | * | 8/2016 | ............. | A47C 15/00 |
| WO | WO-2009022938 A1 | * | 2/2009 | ............. | A47C 9/005 |

*Primary Examiner* — Rodney B White

(74) *Attorney, Agent, or Firm* — Temmerman Law; Mathew J. Temmerman

(57) ABSTRACT

A surgeon support system comprising a base having a foot platform with an appropriate angle adapted to support a user's feet. The base surface may be lifted using a jack pedal and the height is adjusted by a base handle. A knee pad is supported by a knee support bar which is attached to the base. The knee pad is pivotally connected to a seat pad and a chest pad support bar. The seat pad is supported by a seat pad height-adjusting strut and the height is adjustable by a seat pad height-adjusting handle. The chest pad support bar supports a chest pad for forward and backward movement of the user. The angle position of the chest pad is adjusted and released by an angle-adjusting knob on a chest pad angle-adjusting bar. The surgeon support system stabilizes a user close to a workspace for extended periods of time.

19 Claims, 7 Drawing Sheets

(56) References Cited

U.S. PATENT DOCUMENTS

| | | | | |
|---|---|---|---|---|
| 5,490,716 A * | 2/1996 | Naughton | A47C 9/005 | 297/423.12 X |
| 5,545,177 A * | 8/1996 | Coseo | A61H 39/04 | 601/107 |
| 5,971,485 A * | 10/1999 | Clark | A61G 13/009 | 297/423.11 X |
| 6,065,808 A * | 5/2000 | Tinsley | A47C 9/005 | 297/423.11 X |
| 6,543,853 B1 * | 4/2003 | Splane, Jr. | A47C 9/005 | 297/423.11 X |
| 6,595,589 B2 * | 7/2003 | Cochran | A47C 9/002 | 297/423.11 X |
| 6,698,831 B2 * | 3/2004 | Lloyd | A47C 9/005 | 297/423.11 X |
| 6,729,690 B2 * | 5/2004 | Roleder | A47C 9/005 | 297/423.12 X |
| 6,769,736 B2 * | 8/2004 | Roleder | A47C 9/005 | 297/423.12 X |
| 7,144,080 B2 * | 12/2006 | Lloyd | A47C 9/005 | 297/423.12 X |
| 7,367,623 B2 * | 5/2008 | Tholkes | A47C 9/005 | 297/423.11 X |
| 7,878,513 B2 * | 2/2011 | Damouzehtash | A47C 9/027 | 297/423.11 X |
| 9,205,008 B2 * | 12/2015 | Meiki | A61G 13/009 | |
| 9,844,271 B2 * | 12/2017 | Zager | A47C 9/025 | |
| 10,117,510 B2 * | 11/2018 | Rehkemper | A47B 13/16 | |
| 10,342,355 B2 * | 7/2019 | Derecktor | A47C 7/5066 | |
| 2003/0168899 A1 * | 9/2003 | Voyce, IV | A47C 16/04 | 297/423.11 |
| 2014/0265496 A1 * | 9/2014 | Magelund | A61B 90/60 | 297/313 |
| 2014/0265497 A1 * | 9/2014 | Hough | A61G 5/006 | 297/316 |
| 2015/0075575 A1 * | 3/2015 | Karlovich | A61N 1/0452 | 297/217.1 X |
| 2019/0307255 A1 * | 10/2019 | Derecktor | A47C 7/5066 | |
| 2020/0015595 A1 * | 1/2020 | Du | A47C 9/005 | |
| 2020/0016018 A1 * | 1/2020 | Du | A61G 15/10 | |
| 2020/0085198 A1 * | 3/2020 | Derecktor | A47C 9/005 | |
| 2021/0121615 A1 * | 4/2021 | Boddie | A47C 7/622 | |

* cited by examiner

SURGEON SUPPORT SYSTEM

This application claims the benefit of U.S. provisional patent application 62/798,458 and filed Jan. 29, 2019. The disclosure of that provisional application is incorporated herein as if set out in full.

BACKGROUND OF THE DISCLOSURE

Technical Field of the Disclosure

Description of the Related Art

Surgical tools and related systems support a surgeon during the performance of specific actions or carrying out desired effects during a surgery and/or other clinical procedures. The practice of surgery and other clinical procedures often requires extended periods of standing and leaning forward while focusing on a critical task at hand. These extended periods can cause strain associated with leaning, bending, holding one's arms extended and even standing in one place unsupported for hours without rest. Several surgeon support systems are known in the art that have been developed to overcome some of these issues. Many existing support devices will stabilize and prop up separate body parts such as an arm, so that the worker may maintain a given position during extended procedures.

One such device is the herein disclosed Scandinavian kneeling chair, which supports a user in a generally upright position during extended work procedures. This kneeling chair, having seats and support stands, provides support to the body of the user during work. These types of chairs support the bodyweight only when the user is in the sitting position. However, these chair types do not support the body weight of the user while the user is in a standing position, such as for performing a surgery or other clinical procedures that require the user to remain in the same posture for long durations. Also, this chair fails to alleviate/eliminate issues with muscle fatigue caused as a result of maintaining a standing position for an extended period of time.

Currently available massage chairs are designed as a typical chair that provides body support to the user while the user is leaning forward. These types of chairs allow the user to lay forward while receiving a massage. However, the body positioning is necessarily lower in height than is required to perform a typical procedure. Furthermore, the available positions do not necessarily provide the freedom to the user's arms and hands that would be required during procedures and operations. Similarly, strap support systems comprising supporting bands are another existing solution. While the bands support the knee of the user during use, only the knees are supported. Further, in use the user may find themselves in a particular position that can make it difficult to utilize the hands and arms. The strap does not support and maintain the body weight of the user during the procedure of the work for an extended period of time.

There is thus a need for a surgeon support system for surgeons and other workers, such as production/factory workers, who must lean forward and work for long durations of time. Such a needed surgeon support system would include a chest pad to allow the user to position herself towards the workspace so the user may use their hands easily and perform tasks. Further, such a supporting system would support the entire body weight of a user and better fit the user during a procedure requiring a surgeon to lean forward. Such a support system would reduce muscle fatigue and be highly efficient, portable and reliable. The disclosed embodiments below overcome these shortcomings by accomplishing the herein described objectives.

SUMMARY OF THE DISCLOSURE

To minimize the limitations found in the existing systems and methods, and to minimize other limitations that will be apparent upon the reading of this specification, a preferred embodiment of the present invention provides a surgeon support system that allows a user to perform work with his or her hands and arms while leaning forward for an extended duration of time.

The surgeon support system comprises an elevating base having a foot platform with an appropriate angle for the user's feet. The system comprises a plurality of wheels and a brake lock to both allow the elevating base to move, and to lock and prevent the base from moving sideways or forward and backward unintentionally. The elevating base surface may be lifted using conventional means, such as a jack pedal. The height is adjustable by a base handle. A knee pad is supported by a knee support bar which is attached to the elevating base. The knee pad is pivotally connected to a seat pad and a chest pad support bar. The seat pad is supported by a seat pad strut and the height is adjustable by a seat pad height adjust handle. The chest pad support bar supports a chest pad for forwards and backwards movement of the user. The angle position of the chest pad is adjusted and released by an angle adjustment knob on a chest pad angle bar. The chest pad may be adjusted up and down in line with the set angle to accommodate different chest heights. The elevating base surface may further include an encasement housing with a declining top wall and a peripheral foot positioner. A brake lock may further include a lever engaged with the flange of a spring-fixed mount, a knee pad including a friction lip, and a seat pad strut including a pelvic tilting adjustment knob for adjusting pelvic orientation. Further, a chest pad may slide up and down along the plane of the chest of a user. Notably, the angle-adjust knob may include an interconnecting adjustment stem and a plurality of gear notches that may engage with complimentary channels located along a length of stem and/or at the terminal segment of the stem.

It is a first objective of the present embodiment to provide a surgeon support system that allows a user to perform work with the arms or hands while leaning forward for an extended duration of time.

A second objective of the present embodiment is to provide a surgeon support system that allows the surgeon or user to be positioned close to the workspace/patient.

Another objective of the present embodiment is to provide a system that includes additional supports for the arms and head.

Yet another objective of the present embodiment is to provide a surgeon support system that may be used with or without a chest support.

Yet another objective of the present embodiment is to provide a surgeon support system where the wheels may be replaced with tracks or other methods of horizontal movement.

Yet another objective of the present embodiment is to provide a surgeon support system that reduces muscle fatigue and distraction of the user.

Yet another objective of the present embodiment is to provide a surgeon support system that provides foot platforms with appropriate angles for the user's feet.

Yet another objective of the present embodiment is to predictably distribute a user's body weight across several body areas, and to minimize pressure points on any one body area.

Yet another objective of the present embodiment is to provide a system that includes lighting to illuminate the user's workspace.

Yet another objective of the present embodiment is to provide a system that allows a chest pad to fold and/or rotate in and out of the area of use such that it may be utilized temporarily with ease.

Yet another objective of the present embodiment is to provide a system that allows arm supports to fold and/or rotate in and out of the area of use such that they may be utilized temporarily with ease.

Yet another objective of the present embodiment is to provide a system that collapses or folds flat for easy storage when not in use.

Yet another objective of the present embodiment is to provide a system that includes arm supports that are moveable with the user's arms.

Yet another objective of the present embodiment is to provide a system that is motorized and programmable in part or in whole to move various components to new or preset positions.

Yet another objective of the present embodiment is to provide a system that allows the chest pad to pivot in any direction, as with a universal joint.

Yet another objective of the present embodiment is to provide a system comprising a sliding or foldable chest pad that is easily lockable into position by the user.

These and other advantages and features of the present invention are described with specificity so as to make the present invention understandable to one of ordinary skill in the art.

BRIEF DESCRIPTION OF THE DRAWINGS

In order to enhance the clarity and improve understanding of these various elements and embodiments of the invention, elements in the figures have not necessarily been drawn to scale. Furthermore, elements that are known to be common and well understood to those in the relevant art field are not depicted in order to provide a clear view of the various embodiments of the invention. Thus, the drawings are generalized in form in the interest of clarity and conciseness.

FIGS. 7A-8D are diagrammatic depictions of the chest pad in various configurations;

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments by which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an", and "the" include plural referents unless the context clearly dictates otherwise. "And" as used herein is interchangeably used with "or" unless expressly stated otherwise. As used herein, the term "about" means +/−25% of the recited parameter. All embodiments of any aspect of the invention can be used in combination, unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". Words using the singular or plural number also include the plural and singular number, respectively. Additionally, the words "herein", "wherein", "whereas", "above", and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
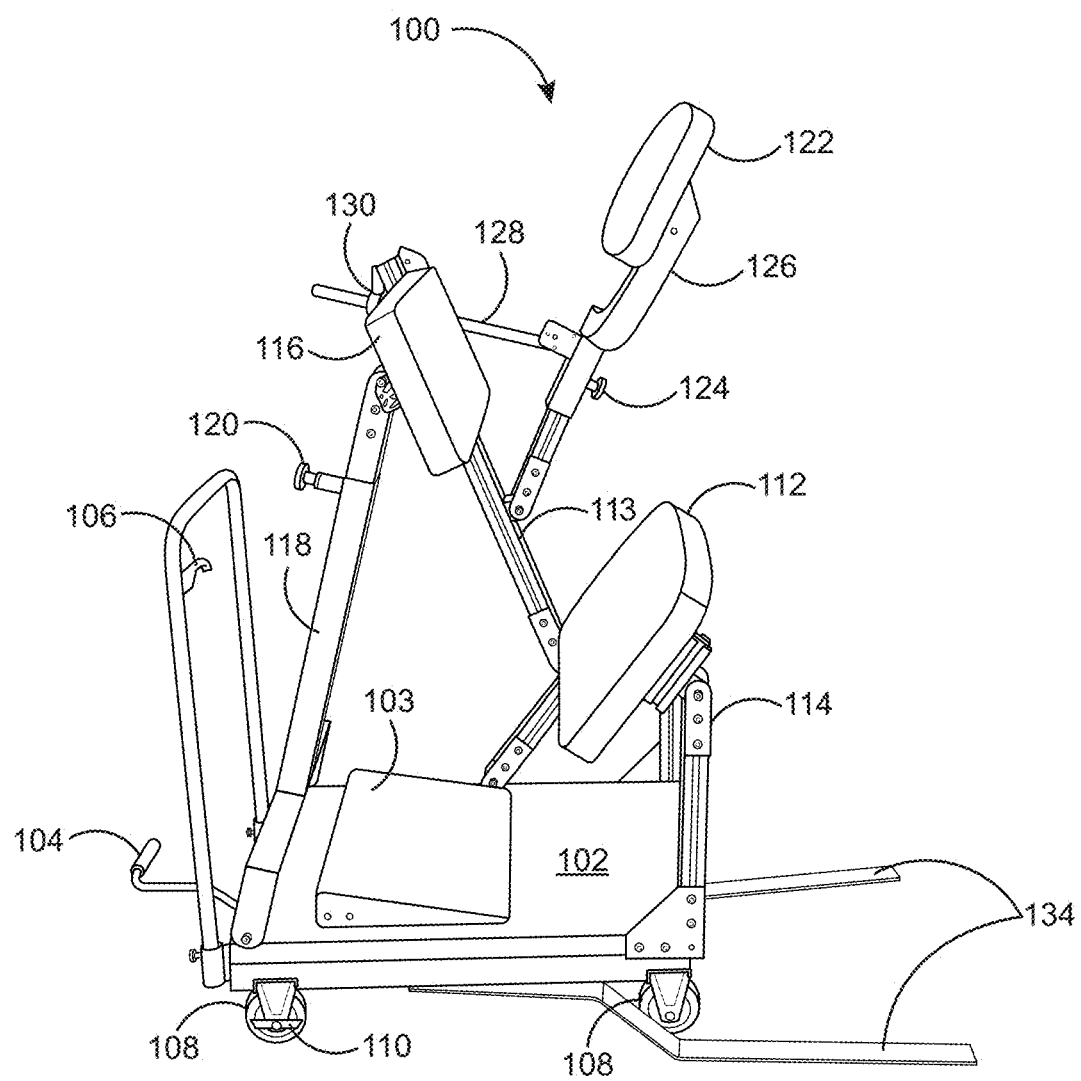
FIG. 1 illustrates a perspective view of a surgeon support system for a surgeon leaning forward and working for extended durations of time in accordance with the preferred embodiment of the present invention.
Figure 2:
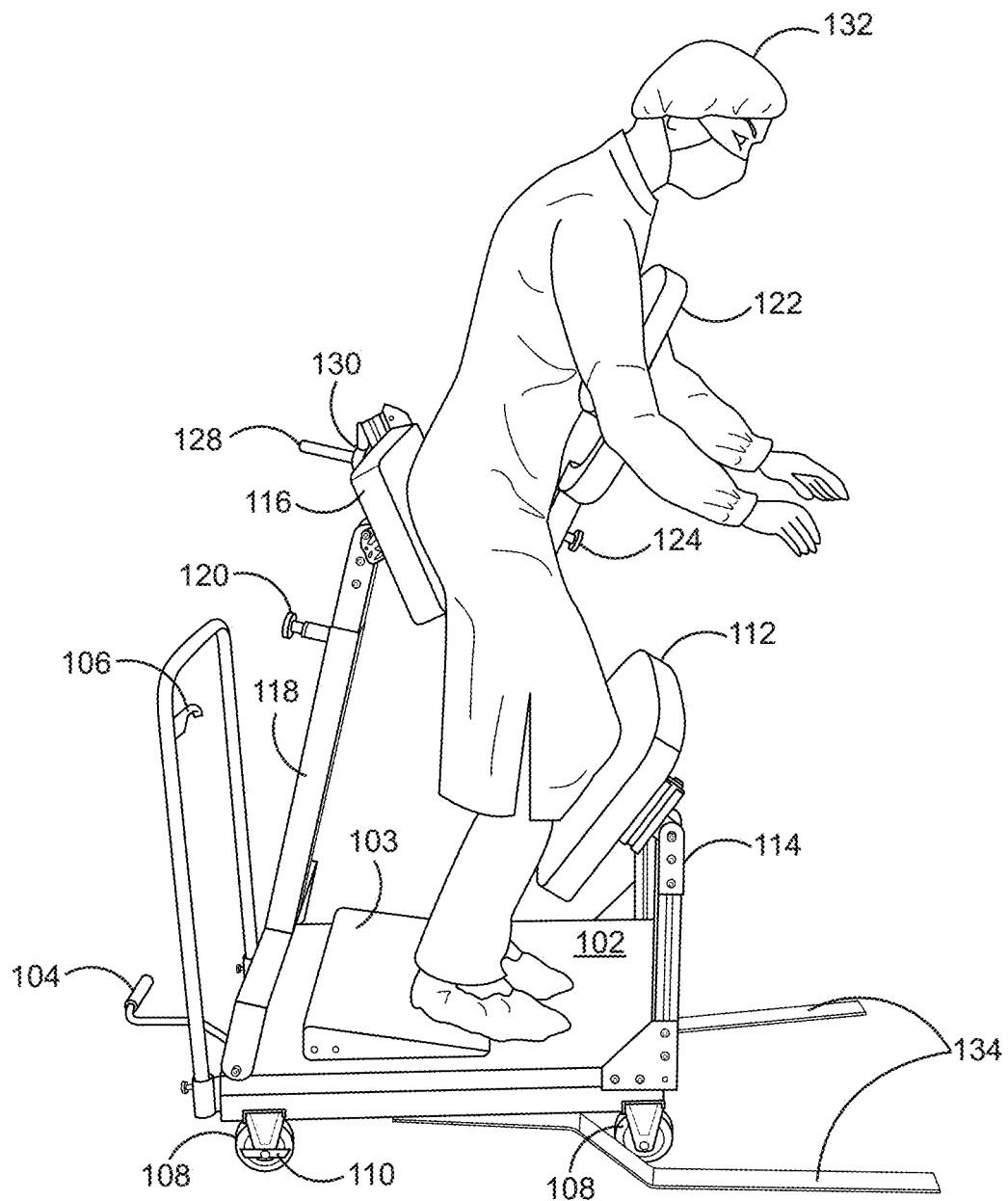
FIG. 2 illustrates a perspective view of the surgeon support system in use in accordance with the preferred embodiment of the present invention.

Referring to FIGS. 1-2, a surgeon support system 100 for a user 132 who in use leans forward and works from the device in accordance with the preferred embodiment of the present invention is illustrated. The surgeon support system 100 of the preferred embodiment provides support to the bodyweight of the user 132 during a surgical procedure. The surgeon support system 100 comprises an elevating base surface 102 having a foot platform 103 with an appropriate angle for the feet of the user 132. The elevating base surface 102 may be lifted using a jack pedal 104 or similar device, and a base handle 106 is used for adjusting the height of the elevating base surface 102 to accommodate various heights of users/surgeons. In other embodiments, the elevating base surface further comprises a cover or encasement housing. In some embodiments, the encasement housing further comprises a declining top wall and a peripheral foot positioner. This expands on the elevating base surface and contemplates a protective covering incorporating additional potential functionality including among others, support for the user's foot during use.

A plurality of wheels 108 is attached to the elevating base surface 102. The plurality of wheels 108 may be locked using a brake lock 110 once the surgeon support system 100 is in the desired location. The brake lock 110 prevents the system 100 from movement on the plurality of wheels 108. The plurality of wheels 108 may be replaced with tracks or other methods of XY movement in alternative embodiments. In other embodiments, the brake lock may further comprise a mechanism by which wheels are forced to lock when a lever is engaged with the flange of a spring-fixed mount.

A knee pad 112 is connected to the elevating base surface 102 by using a knee support bar 114. The knee pad 112 and the knee support bar 114 minimize unnecessary muscle use that causes muscle fatigue and distraction during longer procedures. The knee pad 112 is pivotally or stably connected to the knee pad support bar 114. In some embodiments, the knee pad may further comprise a friction lip allowing for the rotation of the surgeon's foot without inducing torsional compression at the knee, wherein the friction lip is a slight deformation in the knee pad by which a user could more easily engage the knee pad without slippage. The frictioned, lipped, dimpled or other suitable friction providing surface may also be built into any of the pad structures or knobs and touch points of the various embodiments.

The combination of parts distributes the user's bodyweight across multiple body sections, reducing the fatiguing effect of a large amount of body weight on any single section. In addition, the user may actively shift her mass throughout the procedure so that increased or decreased percentages of the user's mass is resting on any given body section. In one embodiment, 30-60% of the weight of a user is distributed to the feet, 10-30% to the knees, 10-40% to the seat, and 0-15% to the chest. In another embodiment, as a percentage of body weight the system may distribute 20-70% weight to the feet, 5-40% to the knees, 5-60% to the seat, and 0-25% to the chest.

The seat pad 116 is connected to the elevating base surface 102 such that the seat pad 116 is supported by a seat pad strut 118, which in turn is located behind the seat pad 116. The seat pad 116 comprises a seat pad height-adjusting handle 120 for adjusting the height of the seat pad 116. The seat pad 116 facilitates positional stability of the user 132 while avoiding unnecessary muscle usage that can lead to fatigue over time. In other embodiments, the seat pad strut may further comprise a pelvic tilting adjustment knob for adjusting pelvic orientation.

Figure 6A:
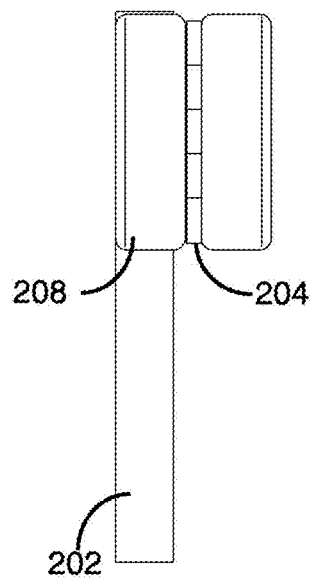
FIG. 6A is a diagrammatic view of the of the surgeon support system wherein the foldable chest pad is in the folded configuration.
Figure 6B:
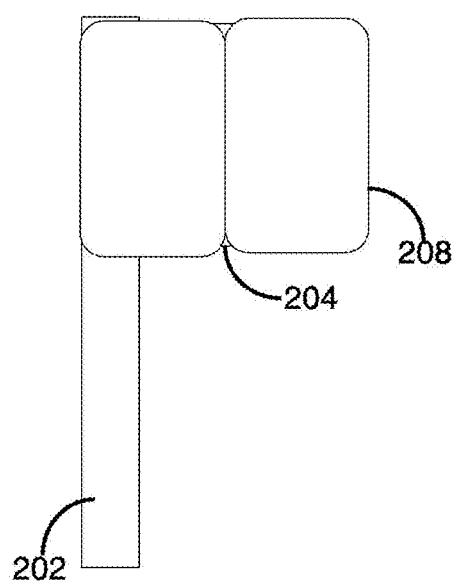
FIG. 6B is a diagrammatic view of the of the surgeon support system wherein the foldable chest pad is in the deployed configuration.

In some embodiments, the chest pad may further comprise a foldable chest pad capable of sliding up and down across the plane of the chest of a user. In the preferred embodiment, the chest pad support bar 126 is used to support a chest pad 122. In some embodiments, the chest pad support bar 126 and chest pad 122 are pivotally connected to the seat support bar 113. The chest pad support bar 126 can move forward and downward or backward and upward using an adjustable spring-loaded grip plate on a rod or a tube. The user 132 may adjust the height of the chest pad 122 using a chest pad height adjust handle 124. In one embodiment, the adjustment is more easily made in one direction only, meaning the user may easily slidably position and lock the chest pad in a desired location without it sliding backwards out of position. This may be configured via a one-way friction fit slide lock or a ratcheting system. Because this allows for the chest pad to be easily positioned, it can be done via the surgeon gripping the chest pad with the forearms, thereby leaving the surgeon's hands free and sterile. As shown in FIG. 6A 6C, the chest pad may further fold and/or rotate in and out of the area of use such that it may be utilized temporarily with ease. Further to the above, the system further comprises a chest pad angle-adjust bar for adjusting the angle position of the chest pad, the chest pad angle-adjust bar having an angle-adjust knob for releasing the angle position of the chest pad attached to the chest pad support bar. In other embodiments, the angle-adjust knob further comprises an interconnecting adjustment stem and a plurality of gear notches that may engage with complimentary channels located along a length of stem and/or at the terminal segment of the stem.

The chest pad support bar 126 allows the surgeon 132 to get close to the work space, so the surgeon 132 can easily use her hands to perform the work by supporting her entire bodyweight during the procedure. The angle position of the chest pad 122 can be adjustable using a chest pad angle bar 128 so it would be easier to maintain a position during extended operations, procedures, and the like. The chest pad angle bar 128 comprises an angle adjustment knob 130, which releases the angle position of the chest pad 122 and is attached to the chest pad support bar 126. In some embodiments the chest pad is affixed to the system via a universal joint that allows the pad to pivot in any direction. In still other embodiments, the chest support may include an internal hinge which provides for a more compact configuration when the support is not in use. Finally, in still other embodiments the device is fitted with arm supports in order to distribute some percentage of the user's body weight across his or her arms. Preferably, the arm supports are foldable such that they may be utilized temporarily with ease.

The system 100 further includes an anti-tipping mechanism, such as a pair of stabilizing fork non-tip levers 134 attached below the elevating base surface 102 to avoid the tipping forward of the system 100.

In this system 100, the user 132 may be any medical physician who performs surgical operations. In other embodiments the user may be any worker who needs to freely use his or her hands while leaning forward for extended periods of time, such as a fine art restorer or artist. The knee, seat, and chest support bars (114, 118, and 126) support the entire bodyweight of the user 132 during the work and allow the user to have full range of motion of arms/hands throughout the procedure. The support bars may comprise T-slotted aluminum or other suitably strong materials. The supporting bars help to position the user 132 closer to the workspace and allows the free movement of the arms/hands during the procedure. The system 100 provides additional supports for the arms and head. The chest pad 122 can be removable where the system 100 can be used with or without the chest pad support.

The surgeon support system 100 is designed for a surgeon 132 or other worker who works on tasks while leaning forward. The system 100 provides support to the bodyweight of the user 132 at the shins or knees, buttocks, feet, and chest and also allows the user 132 to adopt a forward-leaning posture while redistributing the user's bodyweight. The surgeon support system 100 is adaptable to move the user vertically and may additionally be configured to engage a plurality of wheels 108 for ease of forward/back translocation and in alternative embodiments for lateral translocation. In some embodiments, the system 100 may be designed such that it is positioned close to a table or other work surface, thus allowing the user 132 to directly interface with any given task. Further, the surgeon support system 100 of the present invention may provide appropriate counter-balance functionalities to prevent tipping forward of the surgeon support system.

The surgeon support system 100 utilizes the knee pad 112, seat pad 116, and chest pad 122 in order to maximize structural strength and adjustability. Sterility is a general concern during surgery, surgery preparation, post-operative procedures, and the like. It follows that the entire system may be fitted with sterile draping, anti-bacterial coating compositions, or the like in some embodiments. Furthermore, the system may be configured with light sources for illuminating the surgical area and/or sterilizing work surfaces during use. In addition, the system may be motorized and/or programmable in order to move various components to new and/or preset positions, and/or may collapse or fold flat for easy storage when not in use.

Figure 3:
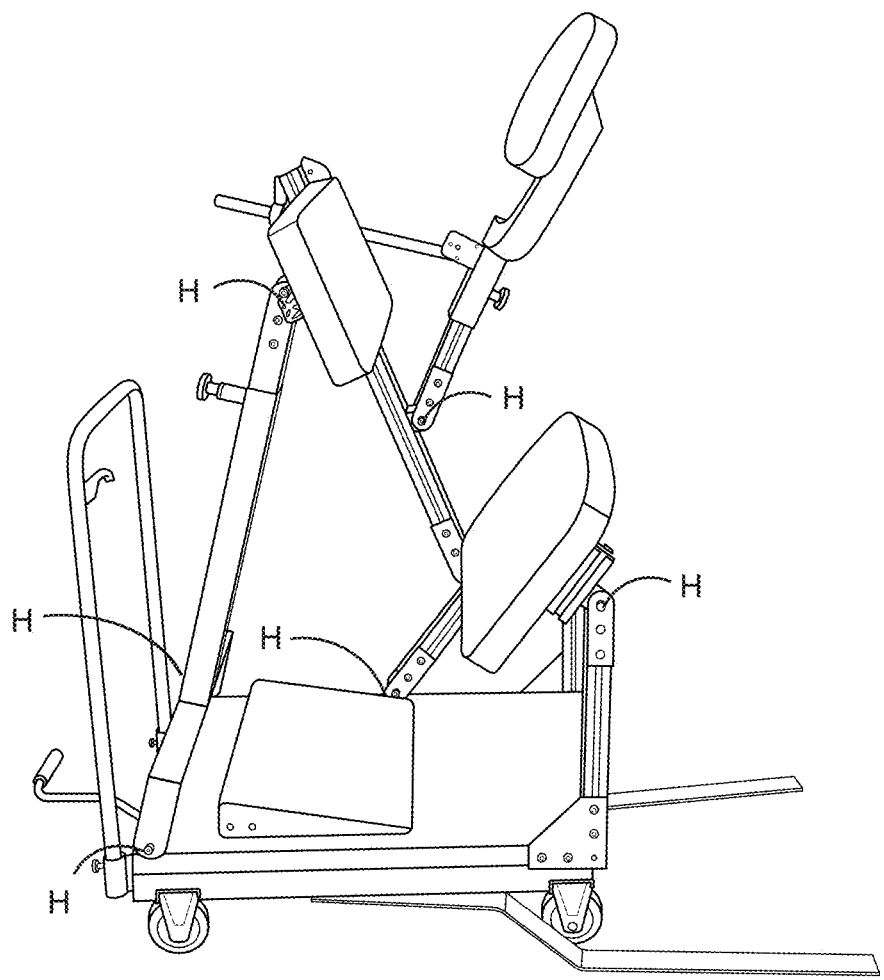
FIG. 3 illustrates a perspective view of the surgeon support system wherein hinge points are marked with an H.
Figure 4:
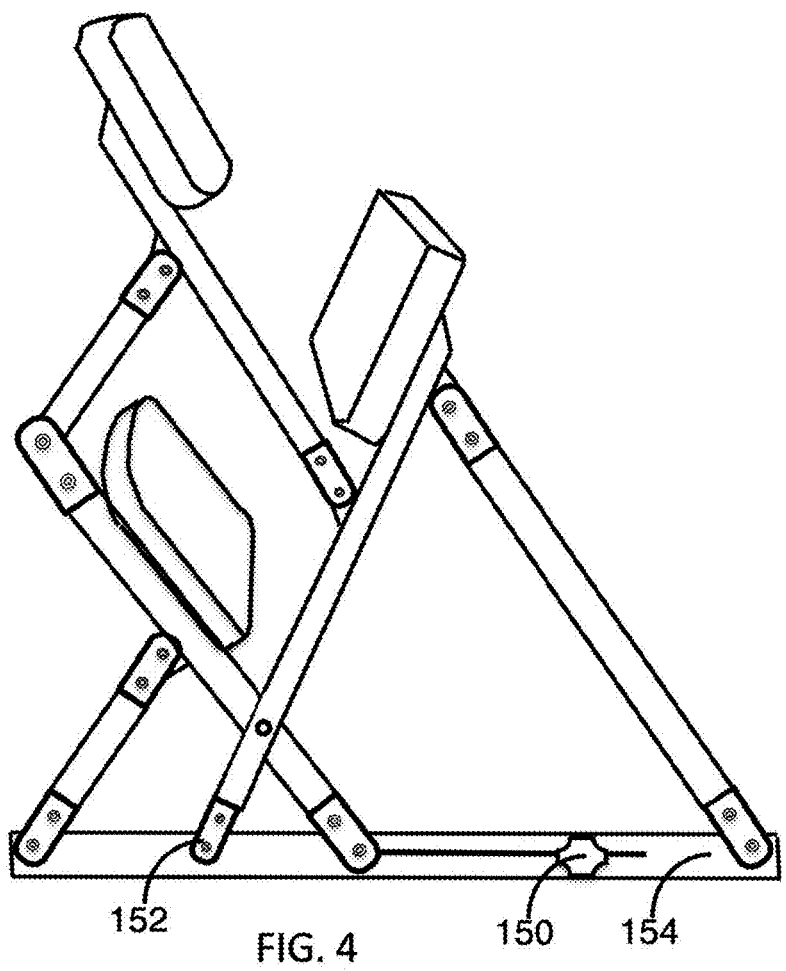
FIGS. 4 and 5 are diagrammatic views of the surgeon support system according to an alternative embodiment of the invention.
Figure 5:
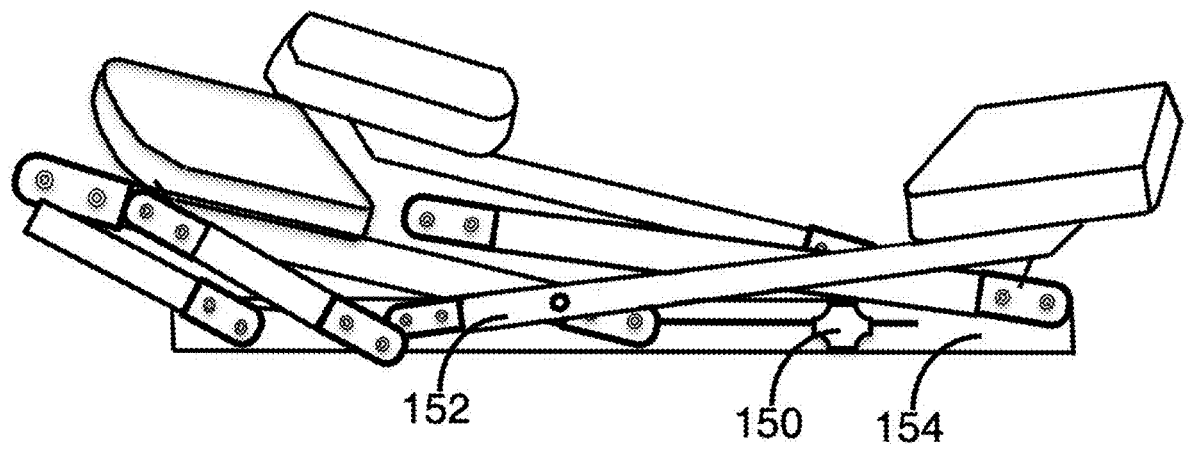

Further, the present system is adaptable to support various hinge/pivot points, user dimensions, and the like. There are several hinge/pivot points, as shown by the label(s) "H" in FIG. 3. In an additional alternative embodiment shown in FIG. 4, a linear actuator 150 attached to the leg base 152 may slide forward and back along the base track 154. The hinged connections shown in FIG. 3 will additionally adjust due to the movement of the leg base 152, thereby providing further overall adjustment for the surgeon and automating the fold-flat nature of the system as described above and shown in FIG. 5. As an added safety feature, the surgeon support system 100 may further include a release mechanism(s) capable of converting the system into a flat configuration.

Figures 7A, 7B, 7C:
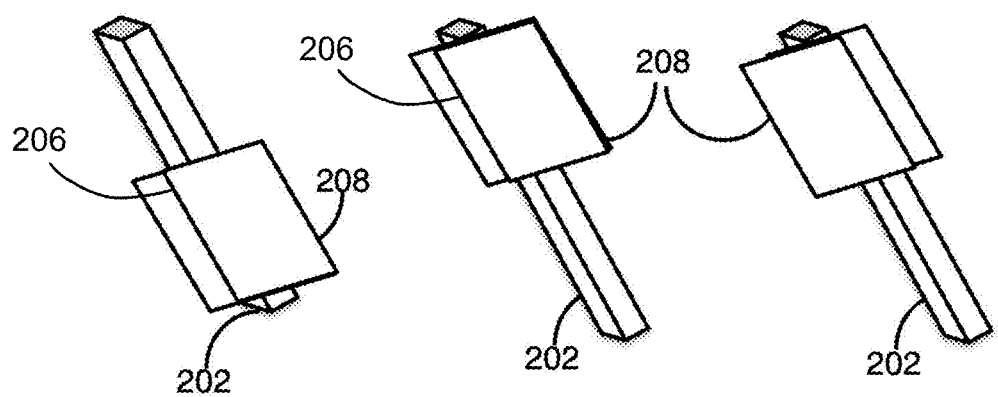
Figure 8A:
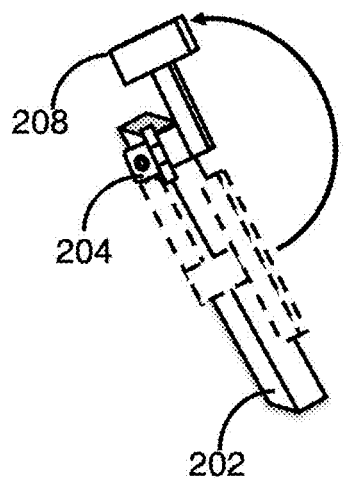
Figure 8B:
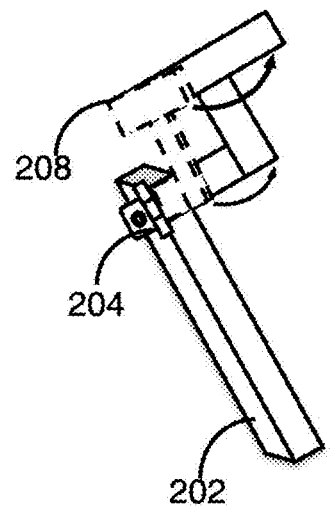
Figure 8C:
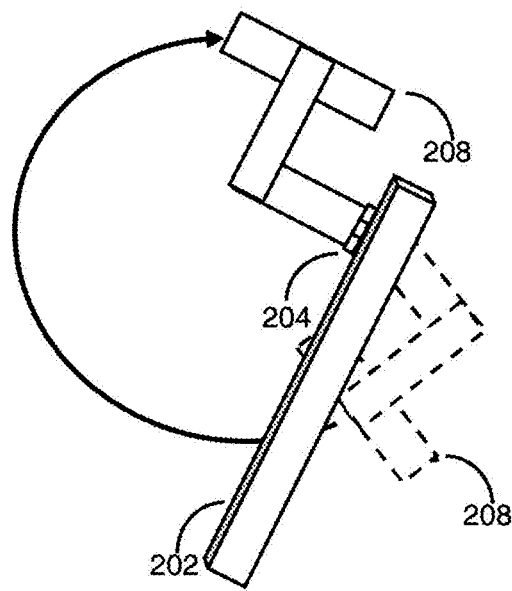
Figure 8D:
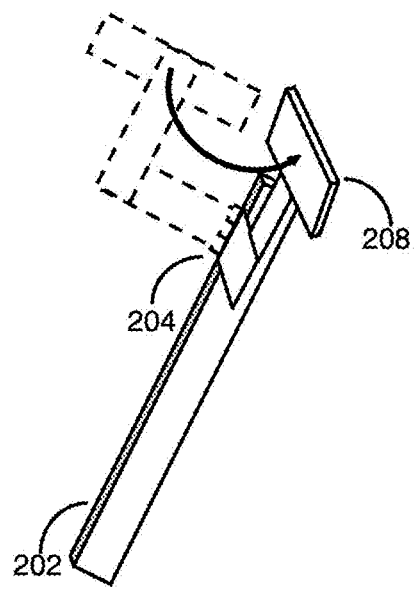

In some embodiments, the present system comprises a side bar 202, chest support hinge 204, foldable chest pad 208, and/or slidable chest support hinge 206, thereby providing a means for a user to foldably manipulate the support system. Generally speaking, these elements combine to enable both a folded position and/or an unfolded position. As depicted in FIGS. 6A-7C, the side bar 202 and slidable chest support hinge 206 allows for the foldable chest pad 208 to slide up and down across the plane of the chest of the user, while the chest support hinge 206 allows for the foldable chest pad 208 to pivot from a folded position to an unfolded position. FIG. 7A shows the chest pad in a first configuration, FIG. 7B shows the chest pad in a deployed configuration, and FIG. 7C shows the chest pad in a folded up configuration, wherein the chest pad has flipped up and to the left to fold out of the way. FIG. 8A shows the chest pad in phantom lines in a first configuration and pivoted to chest height, then moving to a second position wherein it lays down into the plane of the chest to support the chest in FIG. 8B.

Figure 9:
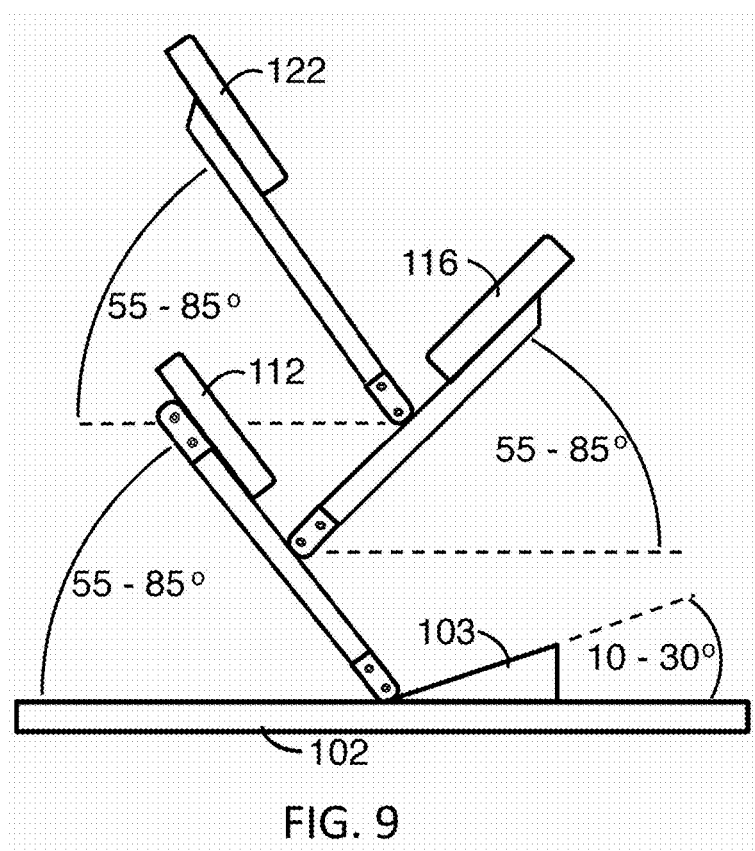
FIG. 9 is a diagrammatic depiction of the preferred embodiment of the invention wherein various component angles are shown.

In use, it is anticipated that certain angles are likely to be formed between components of the device and between body parts of a user who is using the device. Certain exemplary angles internal to the preferred embodiment of the system are shown in FIG. 9. In this figure, the support surfaces may be planar surfaces, or generally planar pads having a rounded appearance but that provide support in an angle normal to the support surface. In this embodiment, the foot pad angle is between 10°-30° and preferably 20°, the knee support angle is between 55°-85°, more preferably between 60°-80°, and most preferably 70°, the seat support angle is between 55°-85°, more preferably between 60°-70°, and most preferably 65°, and the chest support angle is between 55°-85°, more preferably between 60°-80°, and most preferably 70°. All angles described in this paragraph are in reference to horizontal/level, and are the acute angles made between a horizontal or level plane. In some instances this is defined as the plane of the base surface, and the planes of each of said foot pad, seat, knee and chest support are defined by the support pad's major surface that interfaces with its respective base body part.

Figure 10:
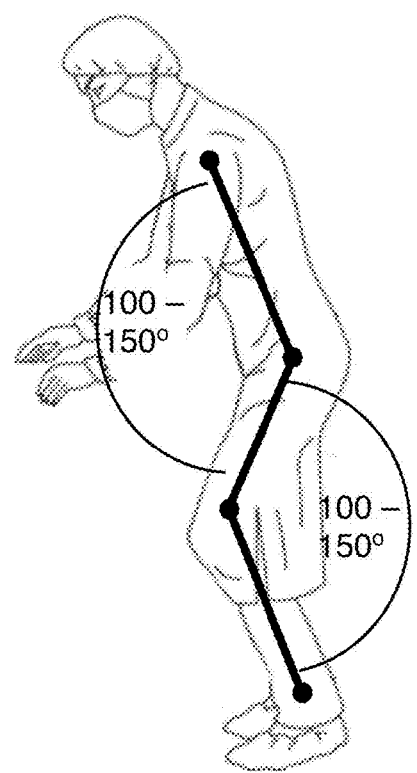
FIG. 10 is a diagrammatic depiction of a human user of the preferred embodiment of the invention wherein various angles between body parts are depicted.

FIG. 10 is a diagrammatic image of a human user without reference to ground, level or horizontal. Here, the internal angle of the user's knee in use is preferably between 100°-150°, more preferably between 110°-140° (not shown), and most preferably 135°. The internal angle of the user's waist is preferably between 125°-160°, more preferably between 130°-150° (not shown), and most preferably 135°.

The foregoing descriptions of the preferred embodiment of the present invention have been presented for the purposes of illustration and description. It is not intended to be exhaustive nor to limit the invention to the precise form disclosed. Many modifications and variations are possible in light of the above teachings. It is intended that the scope of the present invention not be limited by this detailed description, but by the claims and the equivalents to the claims appended hereto.

What is claimed is:

1. A surgeon support system for providing distributed support to the body weight of a user during a procedure for extended durations of time, the system comprising:
   a base surface having a foot platform;
   a plurality of wheels with a brake lock;
   a knee pad supported by at least one knee support bar;
   a seat pad strut for supporting a seat pad;
   a chest pad supported by a laterally-mounted chest pad support bar, whereby the chest pad support bar is pivotally mounted to a seat support bar positioned on the lateral side of the base surface;
   a chest pad angle-adjust bar for adjusting the angle position of the chest pad, the chest pad angle-adjust bar having an angle-adjust actuator for releasing the angle position of the chest pad attached to the chest pad support bar; and
   whereby the chest pad of the surgeon support system provides support to 0-25% body, weight of the user during extended work procedures.

2. The surgeon support system of claim 1, wherein the brake lock further comprises a lever engaged with a flange of a spring-fixed mount.

3. The surgeon support system of claim 1, wherein the knee pad allows for a rotation of the surgeon's foot without inducing torsional compression at the knee.

4. The surgeon support system of claim 1, wherein the seat pad strut allows for adjusting pelvic orientation.

5. The surgeon support system of claim 1, wherein the chest pad further comprises a foldable chest pad configurable to slide up and down across the chest of a user, the chest pad further comprising a chest support hinge and/or a slidable chest support hinge.

6. A surgeon support system for providing distributed support to the body, weight of a user during a procedure for extended durations of time, the system comprising:
   a base surface comprising a foot platform;
   a plurality of wheels with a brake lock attached to the base surface;
   a knee pad with a knee support surface having an angle relative to level of between 55 and 85 degrees, supported by at least one knee support bar attached to the base surface;
   a seat pad providing a seat support surface at an angle relative to level of between 55 and 85 degrees; a seat pad strut for supporting a seat pad, the seat pad strut having a seat pad height-adjusting handle for adjusting the height of the seat pad; and a foldable chest pad supported by a chest pad support bar for the forward and backward movement of the user;

a chest support bar, and one of either a slidable chest support hinge or the foldable chest pad to provide a folded and unfolded position to the surgeon support system;

a chest pad angle-adjust bar for adjusting the angle position of the chest pad, the chest pad angle-adjust bar having an angle-adjust actuator for releasing the angle position of the chest pad attached to the chest pad support bar;

whereby the chest pad of the surgeon support system provides support to 0-25% body weight of the user during extended work procedures.

7. The surgeon support system of claim 6, wherein the base surface is lifted using a jack pedal and height adjusted by a base handle.

8. The surgeon support system of claim 6, further comprising a pair of non-tip levers attached below the base surface to avoid the tipping forward of the system.

9. The surgeon support system of claim 6, wherein the chest pad of the surgeon support system may support 30-60 of the weight of a user.

10. The surgeon support system of claim 6, wherein the brake lock may further comprise a mechanism by which wheels are forced to lock when a lever is engaged with a flange of a spring-fixed mount.

11. The surgeon support system of claim 6, wherein the seat pad strut allows for adjusting pelvic orientation.

12. A surgeon support system for providing distributed support to the body weight of a user during a procedure for extended durations of time, the system comprising:

a base surface comprising a foot platform;

plurality of wheels with a brake lock attached to the base surface;

a knee pad supported by at least one knee support bar attached to the base surface, the knee pad pivotally connected to a seat pad, a seat pad strut for supporting the seat pad, the seat pad strut having a seat pad height-adjusting handle for adjusting the height of the seat pad;

a chest pad supported by a chest pad support bar for the forward and backward movement of the user, the chest pad support bar pivotally mounted to a seat support bar positioned on the lateral side of the base surface; and a chest pad angle-adjust bar for adjusting the angle position of the chest pad, the chest pad angle-adjust bar having an angle-adjust actuator for releasing the angle position of the chest pad attached to the chest pad support bar;

whereby the surgeon support system distributes 30-60% of the weight of a user to the user's feet and 0-15% to the chest; and whereby the chest pad of the surgeon support system provides support to 0-25% body weight of the user during extended work procedures.

13. A surgeon support system for providing distributed support to the body weight of a user during a procedure for extended durations of time, the system comprising:

a base surface having a foot platform, the foot platform providing support to a sole of foot having an angle relative to level of between 10 and 30 degrees;

a plurality of wheels with a brake lock attached to the base surface;

a knee pad with a knee support surface having an angle relative to level of between 55 and 85 degrees;

a seat pad providing a seat support surface at an angle relative to level of between 55 and 85 degrees; and a chest pad supported by a chest pad support bar pivotally mounted to a seat support bar positioned on the lateral side of the base surface, the chest pad having a chest support surface at an angle relative to the level of between 55 and 85 degrees.

14. The surgeon support system of claim 13 wherein the knee pad is supported by at least one knee support bar attached to the base surface.

15. The surgeon support system of claim 13 wherein the angle relative to level of the knee support surface is between 60 and 80 degrees.

16. The surgeon support system of claim 13 wherein the angle relative to level of the seat support surface is between 60 and 80 degrees.

17. The surgeon support system of claim 13 wherein the angle relative to level of the foot support surface is approximately 20 degrees, the angle relative to level of the knee support surface is approximately 70 degrees, and the angle relative to the level of the seat support surface is between 65 and 70 degrees.

18. The surgeon support system of claim 13, wherein the base surface is lifted using a jack pedal and height adjusted by a base handle.

19. The surgeon support system of claim 13 further comprising a pair of non-tip levers attached below the base surface to avoid the tipping forward of the system.

* * * * *